US00PP21851P2

(12) United States Plant Patent
ter Laak

(10) Patent No.: US PP21,851 P2
(45) Date of Patent: Apr. 5, 2011

(54) ***BEGONIA* PLANT NAMED 'SELFOSS'**
(50) Latin Name: *Begonia pendula*
Varietal Denomination: Selfoss

(75) Inventor: Wendela Antoinette ter Laak, Zandvoort (NL)

(73) Assignee: Beekenkamp Plants B.V., Maasdijk (NL)

( * ) Notice: Subject to any disclaimer, the term of this patent is extended or adjusted under 35 U.S.C. 154(b) by 0 days.

(21) Appl. No.: 12/590,023

(22) Filed: Oct. 30, 2009

(51) Int. Cl.
*A01H 5/00* (2006.01)

(52) U.S. Cl. ..... Plt./343
(58) Field of Classification Search ..... Plt./343

See application file for complete search history.

*Primary Examiner*—Susan B McCormick Ewoldt
(74) *Attorney, Agent, or Firm*—C. A. Whealy

(57) ABSTRACT

A new and distinct cultivar of *Begonia* plant named 'Selfoss', characterized by its semi-pendulous and mounded plant habit; freely basal branching habit; relatively small leaves; freely and continuously flowering habit; and single and semi-double flowers that are white in color.

2 Drawing Sheets

Botanical designation: *Begonia pendula.*
Cultivar denomination: 'SELFOSS'.

BACKGROUND OF THE INVENTION

The present invention relates to a new and distinct cultivar of *Begonia* plant, botanically known as *Begonia pendula*, and hereinafter referred to by the name 'Selfoss'.

The new *Begonia* plant is a product of a planned breeding program conducted by the Inventor in Amstelveen, The Netherlands. The objective of the breeding program was to develop new hanging *Begonia* plants with good outdoor performance.

The new *Begonia* plant originated from a cross-pollination made by the Inventor in March, 2005 of a proprietary selection of *Begonia pendula* identified as code number 04-246-05, not patented, as the female, or seed, parent with a proprietary selection of *Begonia pendula* identified as code number 05-H-01, not patented, as the male, or pollen, parent. The new *Begonia* plant was discovered and selected by the Inventor as a single flowering plant from within the progeny of the stated cross-pollination in a controlled greenhouse environment in Amstelveen, The Netherlands in April, 2006.

Asexual reproduction of the new *Begonia* plant by tip cuttings in a controlled greenhouse environment in Amstelveen, The Netherlands since May, 2007, has shown that the unique features of this new *Begonia* plant are stable and reproduced true to type in successive generations.

SUMMARY OF THE INVENTION

Plants of the new *Begonia* have not been observed under all possible environmental conditions. The phenotype may vary somewhat with variations in environment such as temperature and light intensity, without, however, any variance in genotype.

The following traits have been repeatedly observed and are determined to be the unique characteristics of 'Selfoss'. These characteristics in combination distinguish 'Selfoss' as a new and distinct cultivar of *Begonia:*

1. Semi-pendulous and mounded plant habit.

2. Freely basal branching habit.
3. Relatively small leaves.
4. Freely and continuously flowering habit.
5. Single and semi-double flowers that are white in color.

Plants of the new *Begonia* can be compared to plants of the female parent selection. Plants of the new *Begonia* differ from plants of the female parent selection in the following characteristics:

1. Plants of the new *Begonia* are more freely branching than plants of the female parent selection.
2. Plants of the new *Begonia* have single and semi-double flowers whereas plants of the female parent selection have double flowers.
3. Plants of the new *Begonia* have white-colored flowers whereas plants of the female parent selection have yellow-colored flowers.

Plants of the new *Begonia* can be compared to plants of the male parent selection. Plants of the new *Begonia* differ from plants of the male parent selection in the following characteristics:

1. Plants of the new *Begonia* have smaller leaves than plants of the male parent selection.
2. Plants of the new *Begonia* have single and semi-double flowers whereas plants of the male parent selection have double flowers.
3. Plants of the new *Begonia* have greater postproduction longevity than plants of the male parent selection.

Plants of the new *Begonia* can be compared to plants of the *Begonia* 'Victoria Falls', disclosed in U.S. Plant Pat. No. 20,653. In side-by-side comparisons conducted in Amstelveen, The Netherlands, plants of the new *Begonia* differed from plants of 'Victoria Falls' in the following characteristics:

1. Plants of the new *Begonia* were more compact than plants of 'Victoria Falls'.
2. Plants of the new *Begonia* had smaller and darker green-colored leaves than plants of 'Victoria Falls'.
3. Plants of the new *Begonia* had single and semi-double flowers whereas plants of 'Victoria Falls' had double flowers.

4. Tepals of plants of the new *Begonia* were white in color whereas tepals of plants of 'Victoria Falls' were bright orange in color.

Plants of the new *Begonia* can also be compared to plants of the *Begonia* 'Encanto Orange', disclosed in U.S. Plant Pat. No. 20,898. In side-by-side comparisons conducted in Amstelveen, The Netherlands, plants of the new *Begonia* differed from plants of 'Encanto Orange' in the following characteristics:

1. Plants of the new *Begonia* were more rounded leaves than plants of 'Encanto Orange'.
2. Plants of the new *Begonia* had flatter flowers than plants of 'Encanto Orange'.
3. Tepals of plants of the new *Begonia* were white in color whereas tepals of plants of 'Encanto Orange' were bright orange in color.

BRIEF DESCRIPTION OF THE PHOTOGRAPHS

The accompanying colored photographs illustrate the overall appearance of the new *Begonia* plant, showing the colors as true as it is reasonably possible to obtain in colored reproductions of this type. Colors in the photographs may differ slightly from the color values cited in the detailed botanical description which accurately describe the colors of the new *Begonia* plant.

The photograph on the first sheet comprises a side perspective view of a typical flowering plant of 'Selfoss' grown in a container.

The photograph on the second sheet is a close up view of the upper and lower surfaces of typical leaves of 'Selfoss' (left) and the upper surfaces of female and male flowers and the lower surface of a female flower of 'Selfoss' (right).

DETAILED BOTANICAL DESCRIPTIONS

Plants used for the aforementioned photographs and following observations and measurements were grown in Maasdijk, The Netherlands in 19-cm containers and under commercial practice in a glass-covered greenhouse during the spring and early summer. During the production of the plants, day temperatures ranged from 15° C. to 22° C. and night temperatures ranged from 15° C. to 20° C. Plants were 14 weeks old when the photographs and the description were taken. In the following description, color references are made to The Royal Horticultural Society Colour Chart, 2007 Edition, except where general terms of ordinary dictionary significance are used.

Botanical classification: *Begonia pendula* 'Selfoss'.

Parentage:

*Female, or seed, parent.*—Proprietary selection of *Begonia pendula* identified as code number 04-246-05, not patented.

*Male, or pollen, parent.*—Proprietary selection of *Begonia pendula* identified as code number 05-H-01, not patented.

Propagation:

*Type.*—By tip cuttings.

*Time to initiate roots, summer.*—About one week at temperatures of about 20° C. to 25° C.

*Time to initiate roots, winter.*—About one week at temperatures of about 18° C. to 20° C.

*Time to produce a rooted young plant, summer.*—About 32 days at temperatures of about 20° C. to 25° C.

*Time to produce a rooted young plant, winter.*—About 35 days at temperatures of about 18° C. to 20° C.

*Root description.*—Medium in thickness, fibrous; white in color; plants of the new *Begonia* have not been observed to form tubers.

*Rooting habit.*—Moderate branching; moderately dense.

Plant description:

*Plant form and growth habit.*—Semi-pendulous and mounded plant habit; broad inverted triangle; freely basal branching with about six primary branches per plant; primary branches with secondary branches at potentially every node; moderately vigorous growth habit.

*Plant height.*—About 20.9 cm.

*Plant width.*—About 27.3 cm.

*Branch description.*—Length: About 10.7 cm. Diameter: About 7 mm. Internode length: About 1.7 cm. Texture: Smooth, glabrous. Color: Close to N199A tinged with close to 152A.

*Leaf description.*—Arrangement: Alternate, simple. Length: About 10.6 cm. Width: About 5.4 cm. Shape: Ovate. Apex: Acuminate. Base: Reniform, slightly overlapping. Margin: Serrate. Texture, upper surface: Smooth, glabrous; leathery. Texture, lower surface: Sparsely pubescent. Venation pattern: Palmate; reticulate. Color: Developing leaves, upper surface: Between 183A and 200B; venation, close to 144C. Developing leaves, lower surface: Close to 183B; venation, close to 144C. Fully expanded leaves, upper surface: Between 147A and 203A; venation, close to 143A. Fully expanded leaves, lower surface: Close to 183A to 183B; venation, close to 143A to 143B. Petioles: Length: About 6.7 cm. Diameter: About 3 mm. Texture, upper and lower surfaces: Smooth, glabrous. Color, upper and lower surfaces: Close to 185A to 185B.

Flower description:

*Flowering habit.*—Single female and semi-double male rotate flowers arranged in axillary cymes; freely flowering habit with about three to seven open flowers per cyme; about twice as many female flowers as male flowers per plant; flowers and face mostly outwardly or slightly nodding.

*Fragrance.*—Not detected.

*Natural flowering season.*—Plants flower freely and continuously during the late spring until the autumn in The Netherlands.

*Flower longevity.*—Flowers last about ten days on the plant; flowers not persistent.

*Inflorescence height.*—About 15.4 cm.

*Inflorescence diameter.*—About 9.9 cm.

*Flowers.*—Female flowers, diameter: About 4.5 cm. Female flowers, depth (height): About 2.7 cm. Male flowers, diameter: About 5.3 cm. Male flowers, depth (height): About 2.5 cm.

*Flower buds.*—Shape: Flattened orbicular. Length: About 1.5 cm. Diameter: About 1.6 cm. Color: Close to 145D; towards the base, close to 145A to 145B.

*Tepals.*—Arrangement: Rosette. Quantity per flower: Female flowers, usually about five per flower; male flowers, usually about 13 per flower. Length, female flowers: About 2.6 cm. Width, female flowers: About 2.2 cm. Length, male flowers: About 3 cm. Width, male flowers: About 2.2 cm. Shape, female and male flowers: Obovate to orbicular. Apex, female and male flowers: Retuse. Margin, female and male flowers:

Entire. Texture, female and male flowers, upper and lower surfaces: Smooth, glabrous. Color, female and male flowers: When opening, upper surface: Close to 157D; towards the base, close to 150D. When opening, lower surface: Close to 150D; towards the base, close to 150C. Fully opened, upper and lower surfaces: Close to NN155D and tinged with close to 48D; towards the base, close to 8D.

*Tepaloids.*—Arrangement: Rosette. Quantity per flower: Present only on male flowers, usually about ten per flower. Length: About 1.5 cm. Width: About 8 mm. Shape: Irregularly obovate. Apex: Irregularly incised. Margin: Entire. Texture, upper and lower surfaces: Smooth, glabrous. Color: When opening, upper and lower surfaces: Close to 9B to 9C; towards the base, close to 8D to lighter than 8D. Fully opened, upper and lower surfaces: Close to 9C to 9D; towards the base, close to 8D to lighter than 8D.

*Peduncles.*—Angle: About 25° from vertical. Strength: Moderately weak. Length: About 9.6 cm. Diameter: About 4 mm. Texture: Smooth, glabrous. Color: Close to 185A to 185B.

*Pedicels.*—Angle: About 45° from the peduncle. Strength: Moderately weak. Length: About 2.6 cm. Diameter: About 2 mm. Texture: Smooth, glabrous. Color: Close to 146C tinged with close to 185A to 185B.

*Reproductive organs.*—Female flowers: Number of pistils: About six per flower. Pistil length: About 7 mm. Style length: About 2 mm. Style color: Close to 17C to 17D. Stigma color: Close to 17B to 17C. Ovary color: Close to 144B. Male flowers: Number of stamens: About 25 per flower. Filament length: About 3 mm. Filament color: Close to 13C to 13D. Anther length: About 3.5 mm. Anther shape: Flattened triangular. Anther color: Close to 13B. Pollen amount: None observed.

*Seed/fruit.*—Seed and fruit production have not been observed.

Disease/pest resistance: Resistance to pathogens and pests common to *Begonia* has not been observed.

Temperature tolerance: Plants of the new *Begonia* have been observed to tolerate temperatures from about 5° C. to about 35° C.

It is claimed:

1. A new and distinct *Begonia* plant named 'Selfoss' as illustrated and described.

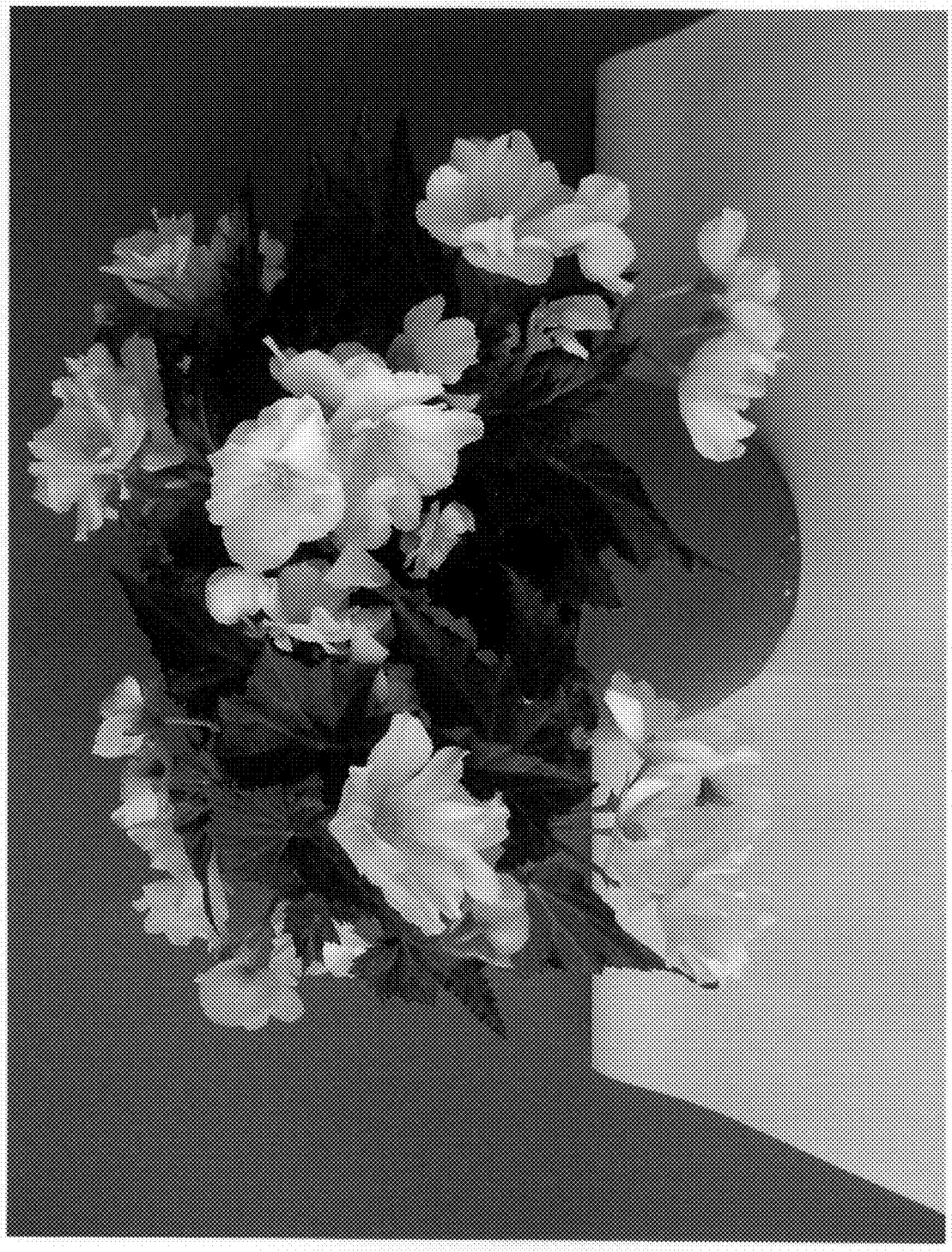

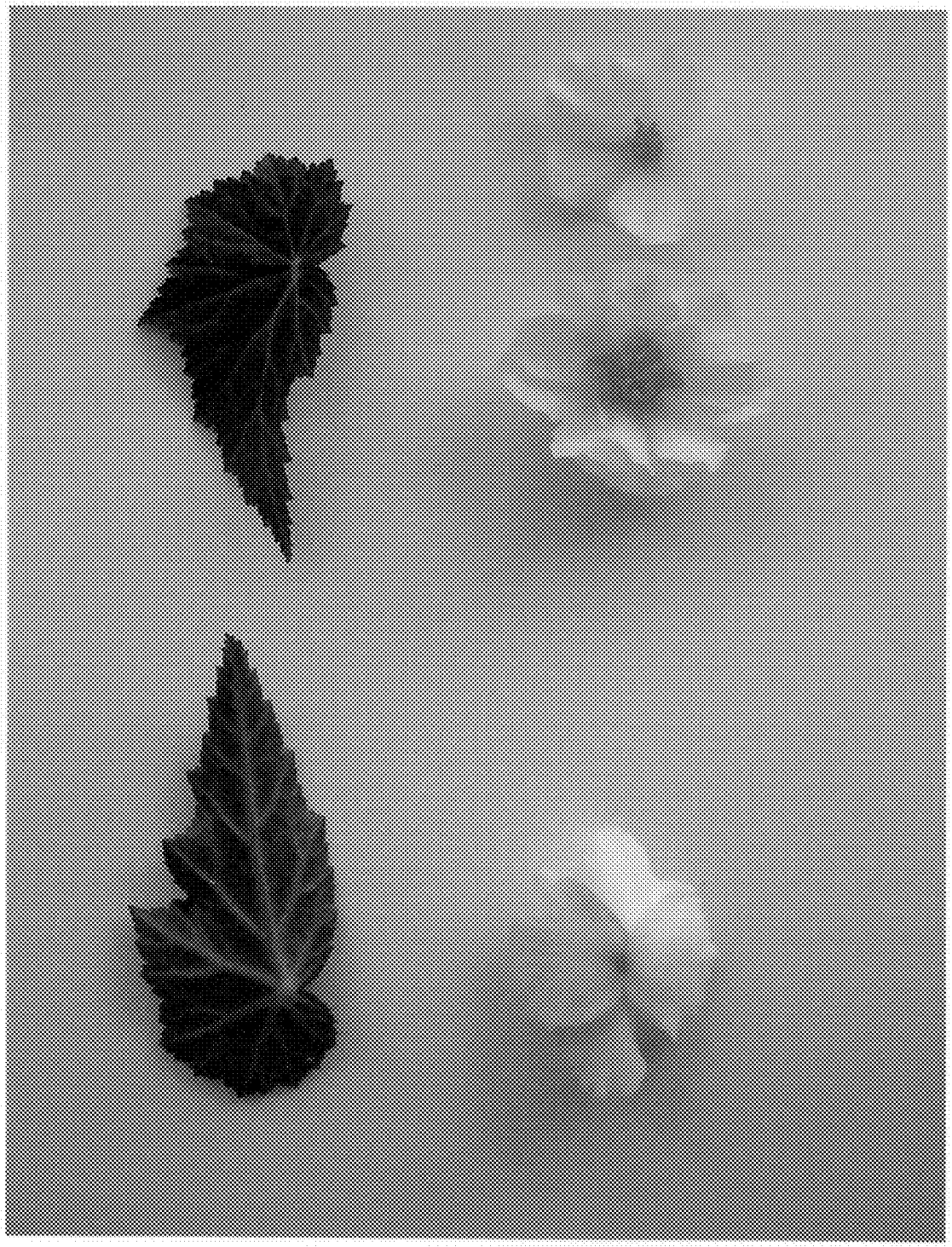

* * * * *